United States Patent
Minagawa

(10) Patent No.: US 10,232,120 B2
(45) Date of Patent: Mar. 19, 2019

(54) GASKET

(71) Applicant: SUMITOMO RUBBER INDUSTRIES, LTD., Kobe-shi, Hyogo (JP)

(72) Inventor: Yasuhisa Minagawa, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 0 days.

(21) Appl. No.: 15/645,120

(22) Filed: Jul. 10, 2017

(65) Prior Publication Data
US 2018/0036490 A1 Feb. 8, 2018

(30) Foreign Application Priority Data
Aug. 8, 2016 (JP) ................... 2016-155942

(51) Int. Cl.
*A61M 5/315* (2006.01)
*F16J 1/00* (2006.01)
*F16J 15/56* (2006.01)
*A61M 5/31* (2006.01)

(52) U.S. Cl.
CPC .......... *A61M 5/31513* (2013.01); *F16J 1/003* (2013.01); *F16J 15/56* (2013.01); *A61M 2005/3101* (2013.01); *A61M 2005/3131* (2013.01)

(58) Field of Classification Search
CPC ...... A61M 5/31513; A61M 2005/3101; A61M 2005/3131; F16J 15/102; F16J 15/104
See application file for complete search history.

(56) References Cited

U.S. PATENT DOCUMENTS

| | | | | |
|---|---|---|---|---|
| 2001/0056264 A1* | 12/2001 | Sayama | ............ | A61M 5/31513 604/218 |
| 2013/0090596 A1* | 4/2013 | Asai | ............ | A61M 5/284 604/89 |
| 2013/0211344 A1* | 8/2013 | Rodriguez | ............ | A61M 5/3129 604/230 |
| 2014/0062036 A1* | 3/2014 | Maeda | ............ | A61M 5/31511 277/615 |
| 2014/0155510 A1* | 6/2014 | Minagawa | ............ | C08J 7/18 522/46 |

(Continued)

FOREIGN PATENT DOCUMENTS

| | | |
|---|---|---|
| JP | 2004-298220 A | 10/2004 |
| JP | 2010-142573 A | 7/2010 |

(Continued)

*Primary Examiner* — Eugene G Byrd
(74) *Attorney, Agent, or Firm* — Birch, Stewart, Kolasch & Birch LLP

(57) ABSTRACT

The present invention provides a gasket excellent in properties such as sliding properties and resistance to liquid leakage. The present invention relates to a gasket having at least two annular projections and at least one annular valley on its sliding surface, the sliding surface being at least partially provided with immobilized polymer chains, the annular projections including a first projection nearest to the top surface and any other projection, the outer diameters of the other projection and the annular valley being in the range of 94 to 98% and 85 to 92%, respectively, with respect to the outer diameter of the first projection taken as 100%.

14 Claims, 1 Drawing Sheet

(56) References Cited

U.S. PATENT DOCUMENTS

| | | | |
|---|---|---|---|
| 2014/0207075 A1* | 7/2014 | Yotsutsuji | A61M 5/3129 604/192 |
| 2014/0339776 A1* | 11/2014 | Nakano | A61M 5/31515 277/358 |
| 2015/0086802 A1* | 3/2015 | Maeda | B29C 43/145 428/519 |
| 2015/0203612 A1* | 7/2015 | Minagawa | C08F 2/50 522/46 |
| 2015/0284487 A1* | 10/2015 | Minagawa | C08J 7/18 522/46 |
| 2016/0033042 A1* | 2/2016 | Minagawa | C10M 107/42 277/654 |

FOREIGN PATENT DOCUMENTS

| | | | | |
|---|---|---|---|---|
| WO | WO-2009128265 A1 * | 10/2009 | | A61M 5/31513 |
| WO | WO-2014038688 A1 * | 3/2014 | | C08F 2/50 |

\* cited by examiner

GASKET

TECHNICAL FIELD

The present invention relates to a gasket.

BACKGROUND ART

In view of the importance of resistance to liquid leakage, elastic bodies such as rubber are used in parts which slide while maintaining a seal, e.g., a gasket which is integrated with a plunger of a syringe and forms a seal between the plunger and the barrel. Unfortunately, such elastic bodies have a slight problem with sliding properties (see Patent Literature 1). To address this problem, a sliding property improving agent, for example silicone oil, is applied to the sliding surface; however, a concern has been raised over the potential adverse effects of silicone oil on recently marketed bio-preparations. On the other hand, gaskets not coated with a sliding property improving agent have inferior sliding properties and therefore do not allow plungers to be smoothly pushed but cause them to pulsate during administration. This results in problems such as inaccurate injection amounts and infliction of pain on patients.

To satisfy the conflicting requirements, that is, resistance to liquid leakage and sliding properties, a method of coating surfaces with a self-lubricating PTFE film has been proposed (see Patent Literature 2). Unfortunately, such PTFE films are generally expensive and increase the production cost of processed products, limiting the range of application of the method. Also, products coated with PTFE films might be unreliable when they are used in applications where sliding or similar movement is repeated and durability is therefore required. Furthermore, since PTFE is vulnerable to radiation, PTFE-coated products unfortunately cannot be sterilized by radiation.

CITATION LIST

Patent Literature

Patent Literature 1: JP 2004-298220 A
Patent Literature 2: JP 2010-142573 A

SUMMARY OF INVENTION

Technical Problem

The present invention aims to solve the above problems and provide a gasket excellent in properties such as sliding properties and resistance to liquid leakage.

Solution to Problem

The present invention relates to a gasket, having at least two annular projections and at least one annular valley on its sliding surface, the sliding surface being at least partially provided with immobilized polymer chains, the annular projections including a first projection nearest to a top surface and any other projection, outer diameters of the other projection and the annular valley being in the range of 94 to 98% and 85 to 92%, respectively, with respect to an outer diameter of the first projection taken as 100%.

Preferably, the at least two annular projections include at least three annular projections, including the first projection, a bottom projection nearest to a bottom surface, and an intermediate projection located between the first projection and the bottom projection, and the intermediate projection has a smaller outer diameter than both the first projection and the bottom projection.

Preferably, the first projection has a curved surface portion on both its top and bottom sides, and the curved surface portion on the bottom side has a greater curvature than the curved surface portion on the top side.

Preferably, the first projection has a curved surface portion on both its top and bottom sides, and the curved surface portion on the top side has a curvature of 0.1 to 0.4.

Preferably, the other projection has a curved surface portion on both its top and bottom sides, and the curved surface portion has a curvature of 0.2 to 0.8.

Preferably, the annular valley has a curved surface portion, and the curved surface portion has a curvature of 0.4 to 2.0.

Preferably, the first projection has an annular flat portion having a width of 0.05 to 0.3 mm.

The polymer chains are preferably immobilized by a surface modification method including: step 1 of forming polymerization initiation points A on a surface of a gasket base material; and step 2 of radically polymerizing a monomer starting from the polymerization initiation points A to grow polymer chains.

The surface modification method preferably includes: step 3 of extending each polymer chain grown in step 2 by adding the same or a different polymer chain; or step 3' of attaching a silane compound to a surface of each polymer chain grown in step 2, followed by reaction with a perfluoroether group-containing silane compound to grow a functional polymer chain.

Step 1 preferably includes adsorbing a photopolymerization initiator A onto the surface of the gasket base material, optionally followed by irradiation with LED light having a wavelength of 300 to 450 nm, to form polymerization initiation points A from the photopolymerization initiator A on the surface.

Step 2 preferably includes radically polymerizing a monomer starting from the polymerization initiation points A by irradiation with LED light having a wavelength of 300 to 450 nm to grow polymer chains.

The polymer chains are preferably immobilized by a surface modification method including step I of radically polymerizing a monomer in the presence of a photopolymerization initiator A on a surface of a gasket base material to grow polymer chains.

The surface modification method preferably includes: step II of extending each polymer chain grown in step I by adding the same or a different polymer chain; or step II' of attaching a silane compound to a surface of each polymer chain grown in step I, followed by reaction with a perfluoroether group-containing silane compound to grow a functional polymer chain.

Step I preferably includes radically polymerizing a monomer by irradiation with LED light having a wavelength of 300 to 450 nm to grow polymer chains.

Preferably, a total polymer chain length is 10 to 50,000 nm.

Advantageous Effects of Invention

The gasket of the present invention has at least two annular projections and at least one annular valley on its sliding surface, wherein the sliding surface is at least partially provided with immobilized polymer chains, the annular projections include a first projection nearest to the top surface and any other projection, and the outer diameters of the other projection and the annular valley are in the range of 94 to 98% and 85 to 92%, respectively, with respect to the outer diameter of the first projection taken as 100%. Accordingly, the present invention provides a gasket excellent in properties such as sliding properties and resistance to liquid leakage without applying any sliding property improving agent that can adversely affect chemical liquids, e.g., silicone oil, to the sliding surface.

DESCRIPTION OF EMBODIMENTS

The gasket of the present invention has at least two annular projections and at least one annular valley on its sliding surface. The sliding surface is at least partially provided with immobilized polymer chains. The annular projections include a first projection nearest to the top surface and any other projection. The other projection and the annular valley each have a predetermined outer diameter relative to the outer diameter of the first projection.

In other words, the gasket has a first top projection, and further has any other projection and an annular valley each of which has an outer diameter with a predetermined ratio to the outer diameter of the first projection, and the sliding surface of the gasket is provided with immobilized polymer chains. Such a gasket achieves a high-level, balanced improvement in sliding properties and resistance to liquid leakage.

Exemplary preferred embodiments of the present invention will be described below referring to drawings.

Figure 1:
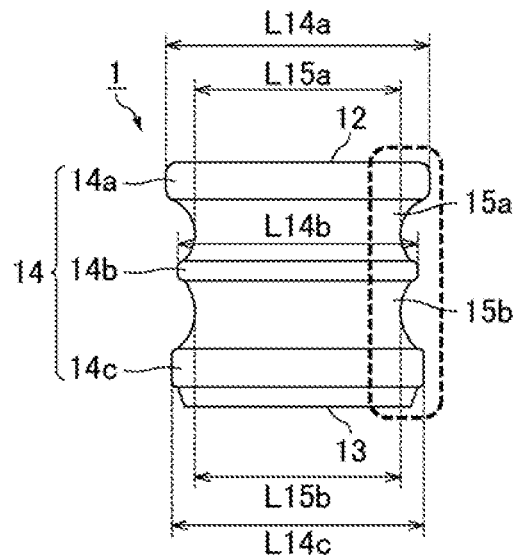
FIG. 1 is an exemplary side view of a gasket base material onto which polymer chains are to be immobilized.

FIG. 1 is an exemplary side view of a base material (gasket base material) onto which polymer chains are to be immobilized.

The present invention can be applied to, for example, a gasket of a syringe that includes a barrel into which liquid is to be injected, a plunger for pushing the injected liquid out of the barrel, and a gasket attached to the tip of the plunger.

In the gasket of the present invention, polymer chains (not shown) are immobilized on at least a part of the sliding surface of a gasket base material 1 as shown in FIG. 1. In the straight cylindrical gasket base material 1 in FIG. 1, the circumference of a top surface 12 on the liquid-contact side and the circumference of a bottom surface 13 to be connected to the tip of a plunger are formed integrally with a sliding portion 14 (cylindrical portion) extending in the height direction (sliding direction).

With regard to the gasket base material 1, the outer periphery of the sliding portion 14 includes three annular projections (at least two annular projections) that make sliding contact with the inner periphery of the peripheral cylindrical portion of the barrel; specifically, a first projection 14a at a position nearest to the top surface 12 (first projection 14a nearest to the top surface), a bottom projection 14c at a position farthest from the top surface 12 (bottom projection 14c nearest to the bottom surface), and an intermediate projection 14b at a position between the projections 14a and 14c (14b and 14c: any other projection). In the gasket base material shown in FIG. 1, the top surface 12 is formed integrally with the first projection 14a.

Although FIG. 1 shows an embodiment having three annular projections, there may be any number of annular projections but at least two. Although the embodiment has one intermediate projection 14b, any projection between the first projection and the bottom projection corresponds to an intermediate projection, and there may be a plurality of intermediate projections. When an intermediate projection (e.g. intermediate projection 14b) is provided, the outer diameter of the intermediate projection is preferably smaller than the outer diameters of the first projection 14b and the bottom projection 14c in order to simultaneously achieve sliding properties and resistance to liquid leakage.

The gasket base material 1 includes annular valleys 15a and 15b (at least one annular valley) in the outer periphery of the sliding portion 14. Although FIG. 1 shows an embodiment having two annular valleys, there may be any number of annular valleys but at least one.

In order to simultaneously achieve sliding properties and resistance to liquid leakage, at least one of the intermediate projection 14b and the bottom projection 14c (any other projection) has an outer diameter L14b or L14c of 94 to 98%, preferably 94 to 97%, with respect to the outer diameter L14a of the first projection 14a taken as 100%. In the present invention, all the other projections preferably have outer diameters falling within the range indicated above. The outer diameters of the first projection 14a, intermediate projection 14b, and bottom projection 14c are the maximum diameters of the respective annular projections.

In order to simultaneously achieve sliding properties and resistance to liquid leakage, at least one of the outer diameter L15a of the annular valley 15a and the outer diameter L15b of the annular valley 15b as shown in FIG. 1 is 85 to 92%, preferably 87 to 91%, with respect to the outer diameter L14a of the first projection 14a taken as 100%. In the present invention, all the annular valleys preferably have outer diameters falling within the range indicated above. The outer diameters of the annular valleys 15a and 15b are the minimum diameters of the respective annular valleys.

Figure 2:
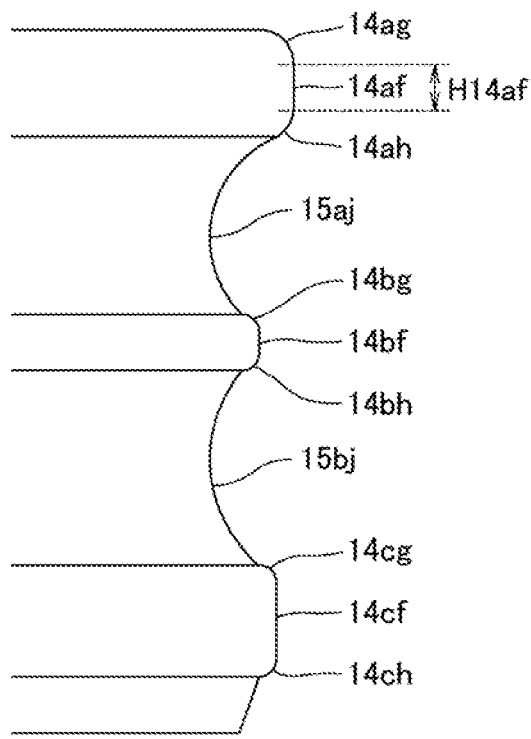
FIG. 2 is an exemplary partially enlarged view of the sliding portion shown in FIG. 1.

FIG. 2 is an exemplary partially enlarged view of the part surrounded by the broken line in FIG. 1, including the first projection 14a, intermediate projection 14b, bottom projection 14c, and annular valleys 15a and 15b.

The sliding contact surface of the first projection 14a includes an annular flat portion 14af (straight cylindrical portion) having a width H14af in the height direction (sliding direction) of the gasket base material 1. The annular flat portion 14af may not be in a perfectly straight cylindrical shape. For use in syringes, for example, the annular flat portion may be in any form that allows it to sufficiently make sliding contact with the inner periphery of the barrel to ensure resistance to liquid leakage. In order to simultaneously achieve sliding properties and resistance to liquid leakage, the width H14af of the annular flat portion 14af is preferably 0.05 to 1.0 mm, more preferably 0.05 to 0.3 mm.

In order to simultaneously achieve sliding properties and resistance to liquid leakage, the sliding contact surface of the first annular projection 14a preferably includes a curved surface portion (top curved surface portion 14ag) extending from the annular flat portion 14af towards the top surface, and a curved surface portion (bottom curved surface portion 14ah) extending from the annular flat portion 14af towards the bottom surface, in addition to the annular flat portion 14af.

In order to simultaneously achieve sliding properties and resistance to liquid leakage, the top curved surface portion 14ag of the annular projection 14a preferably has a curvature of 0.1 to 1.0, more preferably 0.1 to 0.4. The bottom curved surface portion 14ah preferably has a curvature of 0.1 to 1.5, more preferably 0.2 to 0.8. Preferably, the curvature of the bottom curved surface portion 14*ah* is equal to or greater than that of the top curved surface portion 14*ag*. More preferably, the curvature of the bottom curved surface portion 14*ah* is greater than that of the top curved surface portion 14*ag*.

In order to simultaneously achieve sliding properties and resistance to liquid leakage, the intermediate projection 14*b* and the bottom projection 14*c* (any other projection) have top curved surface portions 14*bg* and 14*cg*, respectively, and bottom curved surface portions 14*bh* and 14*ch*, respectively. The curvatures of the top curved surface portions 14*bg* and 14*cg* and the bottom curved surface portions 14*bh* and 14*ch* are each preferably 0.1 to 1.5, more preferably 0.2 to 0.8.

In order to simultaneously achieve sliding properties and resistance to liquid leakage, the annular valleys 15*a* and 15*b* may suitably have curved surface portions 15*aj* and 15*bj*, respectively. In this case, the curvatures of the curved surface portions 15*aj* and 15*bj* are each preferably 0.1 to 2.0, more preferably 0.4 to 2.0. Although FIG. 2 shows an embodiment in which each of the annular valleys 15*a* and 15*b* is formed of a single curved surface portion, other embodiments may also be used in which, for example, the annular valley has curved surface portions (formed in the direction toward which the outer diameter decreases) at the upper and lower ends thereof, and both curved surface portions are connected via an annular flat portion.

As described above, the gasket of the present invention has at least two annular projections and at least one annular valley on its sliding surface, and the sliding surface is at least partially provided with immobilized polymer chains. Non-limiting examples of the polymer chains include polymer chains formed by polymerization of conventionally known monomers. The polymer chains may be immobilized by any method, and known methods may be used, such as the "grafting from" method in which graft polymerization of monomers is initiated from the surface and the "grafting to (on)" method in which polymer chains are reacted with and immobilized onto the surface.

Such a gasket of the present invention can be prepared, for example, by subjecting a gasket base material having at least two annular projections and at least one annular valley on its sliding surface to a surface modification method as described below.

The gasket of the present invention may be prepared by immobilizing polymer chains by a surface modification method that includes step 1 of forming polymerization initiation points A on the surface of a gasket base material, and step 2 of radically polymerizing a monomer starting from the polymerization initiation points A to grow polymer chains.

Step 1 includes forming polymerization initiation points A on the surface of a vulcanized rubber or a formed thermoplastic elastomer (gasket base material).

The vulcanized rubber or the thermoplastic elastomer may suitably be one containing a carbon atom adjacent to a double bond (i.e., allylic carbon atom).

Examples of rubbers that can be used include diene rubbers such as styrene-butadiene rubber, polybutadiene rubber, polyisoprene rubber, natural rubber, and deproteinized natural rubber; butyl rubber and halogenated butyl rubbers which have a degree of unsaturation of a few percent of isoprene units; and silicone rubber. In the case of butyl rubber or halogenated butyl rubbers, it is preferably a rubber crosslinked by triazine because the amount of matter extracted from the vulcanized rubber is reduced. In such a case, the rubber may contain an acid acceptor. Suitable examples of the acid acceptor include hydrotalcite and magnesium carbonate.

When other rubbers are used, sulfur vulcanization is preferably performed. In such a case, compounding ingredients commonly used for sulfur vulcanization may be added, such as vulcanization accelerators, zinc oxide, filler, and silane coupling agents. Suitable examples of the filler include carbon black, silica, clay, talc, and calcium carbonate.

The vulcanization conditions for the rubber may be appropriately chosen. The rubber is preferably vulcanized at a temperature of 150° C. or higher, more preferably 170° C. or higher, still more preferably 175° C. or higher.

Examples of thermoplastic elastomers that can be used include polymer compounds that have rubber elasticity at room temperature owing to aggregates of plastic components (hard segments) serving as crosslinking points (e.g., thermoplastic elastomers (TPE) such as styrene-butadiene-styrene copolymer); and polymer compounds having rubber elasticity, obtained by mixing a thermoplastic component and a rubber component and dynamically crosslinking the mixture by a crosslinking agent (e.g., thermoplastic elastomers (TPV) such as polymer alloys containing a combination of a styrenic block copolymer or olefinic resin with a crosslinked rubber component).

Other suitable thermoplastic elastomers include nylon, polyester, polyurethane, polypropylene, fluoroelastomers such as PTEF, and dynamically crosslinked thermoplastic elastomers thereof. Preferred among dynamically crosslinked thermoplastic elastomers are those obtained by dynamically crosslinking a halogenated butyl rubber in a thermoplastic elastomer. In this case, the thermoplastic elastomer used is preferably, for example, nylon, polyurethane, polypropylene, styrene-isobutylene-styrene block copolymer (SIBS).

The polymerization initiation points A may be formed, for example, by adsorbing a photopolymerization initiator A onto the surface of a gasket base material. Examples of the photopolymerization initiator A include carbonyl compounds, organic sulfur compounds such as tetraethylthiuram disulfide, persulfides, redox compounds, azo compounds, diazo compounds, halogen compounds, and photoreductive pigments. Carbonyl compounds are preferred among these.

The carbonyl compound used as a photopolymerization initiator A is preferably benzophenone or its derivative, and may suitably be a benzophenone compound represented by the following formula:

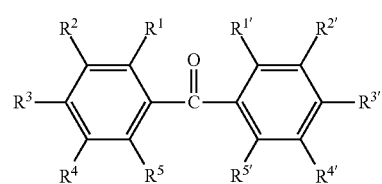

wherein $R^1$ to $R^5$ and $R^{1'}$ to $R^{5'}$ are the same as or different from one another and each represent a hydrogen atom, an alkyl group, a halogen (fluorine, chlorine, bromine, or iodine), a hydroxy group, a primary to tertiary amino group, a mercapto group, or a hydrocarbon group optionally containing an oxygen atom, a nitrogen atom, or a sulfur atom; and any adjacent two of $R^1$ to $R^5$ and $R^{1'}$ to $R^{5'}$ may be joined to each other to form a cyclic structure together with the carbon atoms to which they are attached.

Specific examples of the benzophenone compound include benzophenone, xanthone, 9-fluorenone, 2,4-dichlorobenzophenone, methyl o-benzoylbenzoate, 4,4'-bis(dimethylamino)benzophenone, and 4,4'-bis(diethylamino)benzophenone. Benzophenone, xanthone, and 9-fluorenone are particularly preferred among these because they allow polymer brushes to be well formed.

Other suitable examples of the benzophenone compound include fluorobenzophenone compounds, such as 2,3,4,5,6-pentafluorobenzophenone and decafluorobenzophenone respectively represented by the following formulas.

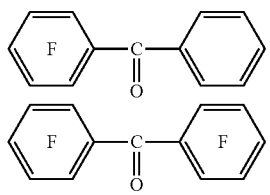

Thioxanthone compounds can also be suitably used as the photopolymerization initiator A because they provide a high polymerization rate and also can easily be adsorbed onto and/or reacted with rubber or the like. For example, compounds represented by the following formula can be suitably used.

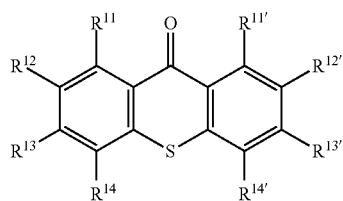

In the formula, $R^{11}$ to $R^{14}$ and $R^{11'}$ to $R^{14'}$ are the same as or different from one another and each represent a hydrogen atom, a halogen atom, an alkyl group, a cyclic alkyl group, an aryl group, an alkenyl group, an alkoxy group, or an aryloxy group.

Examples of thioxanthone compounds represented by the above formula include thioxanthone, 2-isopropylthioxanthone, 4-isopropylthioxanthone, 2,3-diethylthioxanthone, 2,4-diethylthioxanthone, 2,4-dichlorothioxanthone, 2-methoxythioxanthone, 1-chloro-4-propoxythioxanthone, 2-cyclohexylthioxanthone, 4-cyclohexylthioxanthone, 2-vinylthioxanthone, 2,4-divinylthioxanthone, 2,4-diphenylthioxanthone, 2-butenyl-4-phenylthioxanthone, 2-methoxythioxanthone, and 2-p-octyloxyphenyl-4-ethylthioxanthone. Preferred among these are those which are substituted at one or two, particularly two, of $R^{11}$ to $R^{14}$ and $R^{11'}$ to $R^{14'}$ with alkyl groups. More preferred is 2,4-diethylthioxanthone.

The photopolymerization initiator A such as a benzophenone or thioxanthone compound can be adsorbed onto the surface of the gasket base material by conventionally known methods. For example, in the case of a benzophenone or thioxanthone compound, the benzophenone or thioxanthone compound is dissolved in an organic solvent to prepare a solution, and a surface portion of the gasket base material to be modified is treated with this solution so that the compound is adsorbed onto the surface, optionally followed by evaporating off the organic solvent by drying, to form polymerization initiation points. The surface may be treated by any method that allows the solution of the benzophenone or thioxanthone compound to be brought into contact with the surface of the gasket base material. Suitable examples of the surface treatment method include application or spraying of the benzophenone or thioxanthone compound solution; and immersion into the solution. When only a part of the surface needs to be modified, it is sufficient to adsorb the photopolymerization initiator A only onto such a part of the surface. In this case, for example, application or spraying of the solution is suitable. Examples of the solvent include methanol, ethanol, acetone, benzene, toluene, methyl ethyl ketone, ethyl acetate, and THF. Acetone is preferred because it does not swell the gasket base material and it rapidly dries and evaporates off.

After the portion onto which polymer chains are to be immobilized is surface treated with the benzophenone or thioxanthone compound solution so that the photopolymerization initiator A is adsorbed onto the surface, the surface of the gasket base material is preferably further irradiated with light so that the polymerization initiator A is chemically bonded to the surface. For example, the benzophenone or thioxanthone compound may be immobilized on the surface by irradiation with ultraviolet light having a wavelength of 300 to 450 nm, preferably 300 to 400 nm, more preferably 350 to 400 nm. During step 1 and the immobilization, a hydrogen atom is abstracted from the rubber surface and a carbon atom on the rubber surface is then covalently bonded to the carbon atom in C=O of benzophenone while the abstracted hydrogen atom is bonded to the oxygen atom in C=O to form C—O—H, as shown in the scheme below. Moreover, since this hydrogen abstraction reaction selectively occurs on allylic hydrogen atoms in the gasket base material, the rubber preferably contains a butadiene or isoprene unit that contains an allylic hydrogen atom.

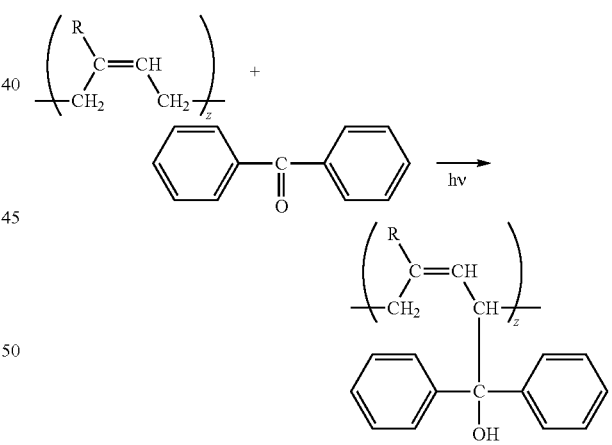

R: a hydrogen atom or a C1-C4 alkyl group

In particular, the polymerization initiation points A are preferably formed by treating the surface of the gasket base material with the photopolymerization initiator A so that the photopolymerization initiator A is adsorbed onto the surface, and then irradiating the treated surface with LED light having a wavelength of 300 to 450 nm. Particularly preferably, after the surface of the gasket base material is treated with the benzophenone or thioxanthone compound solution so that the photopolymerization initiator A is adsorbed, the treated surface is further irradiated with LED light having a wavelength of 300 to 450 nm so that the adsorbed photopolymerization initiator A is chemically bonded to the surface. Since light having a wavelength of less than 300 nm may break and damage the molecules in the gasket base material, light having a wavelength of 300 nm or more is preferably used. Light having a wavelength of 355 nm or more is more preferred in that such light causes only very small damage to the gasket base material. Also, since light having a wavelength of more than 450 nm is less likely to activate the polymerization initiator and thus less likely to allow the polymerization reaction to proceed, light having a wavelength of 450 nm or less is preferred. Light having a wavelength of 400 nm or less is more preferred for greater activation of the polymerization initiator. LED light having a wavelength of 355 to 380 nm is particularly suitable. Although LED light is suitable because the wavelength range of LED light is narrow so that no wavelengths other than the center wavelength are emitted, mercury lamps or other light sources can also achieve similar effects to those of LED light if a filter is used to block light with wavelengths less than 300 nm.

Step 2 includes radically polymerizing a monomer starting from the polymerization initiation points A to grow polymer chains.

Non-limiting examples of the monomer include hydroxyalkyl (meth)acrylates such as hydroxyethyl (meth)acrylate and hydroxybutyl (meth)acrylate, (meth)acrylic acid, dimethyl (meth)acrylamide, diethyl (meth)acrylamide, isopropyl (meth)acrylamide, hydroxyethyl (meth)acrylamide, methoxymethyl (meth)acrylamide, (meth)acrylamide, methoxymethyl (meth)acrylate, and (meth)acrylonitrile. These monomers may be used alone or in combinations of two or more. In particular, from the standpoint of cost efficiency, the monomer to be used in step 2 is preferably (meth)acrylic acid, a hydroxyalkyl (meth)acrylate, dimethyl (meth)acrylamide, diethyl (meth)acrylamide, isopropyl (meth)acrylamide, hydroxyethyl (meth)acrylamide, methoxymethyl (meth)acrylamide, (meth)acrylamide, or methoxymethyl (meth)acrylate, more preferably (meth)acrylic acid or (meth)acrylamide, still more preferably acrylic acid or acrylamide.

Fluorine-containing monomers may also be suitably used as the monomer.

Examples of fluorine-containing monomers include fluorine-containing (meth)acrylic-modified organosilicon compounds and cyclic siloxanes. Preferred among fluorine-containing monomers are monomers containing a perfluoropolyether group because they allow the effects of the present invention to be better achieved.

The fluorine-containing monomer may suitably be, for example, a fluorine-containing (meth)acrylic-modified organosilicon compound produced by an addition reaction of (B) an unsaturated monocarboxylic acid containing a (meth)acrylic group with (A) a fluorine-containing epoxy-modified organosilicon compound represented by the following formula (1):

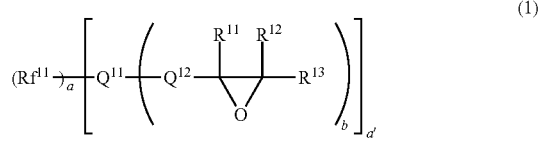

(1)

wherein $Rf^{11}$ represents a monovalent or divalent group having a molecular weight of 100 to 40,000 and containing a fluoroalkyl structure or a fluoropolyether structure; $Q^{11}$ represents an (a+b)-valent linking group containing at least (a+b) silicon atoms and having a siloxane structure, an unsubstituted or halogen-substituted silalkylene structure, a silarylene structure, or a combination of two or more thereof, and $Q^{11}$ may form a cyclic structure; $Q^{12}$ represents a C1-20 divalent hydrocarbon group which may form a cyclic structure and may be interrupted by an ether linkage (—O—) or an ester linkage (—COO—); $R^{11}$ to $R^{13}$ each independently represent a hydrogen atom or a C1-10 monovalent hydrocarbon group, provided that a part or all of the hydrogen atoms of $R^{11}$ to $R^{13}$ may be replaced with halogen atoms, and $R^{11}$ and $R^{12}$ may be joined to each other to form a ring together with the carbon atoms to which they are attached; when $Rf^{11}$ is a monovalent group, a' and a represent 1 and an integer of 1 to 6, respectively, and when $Rf^{11}$ is a divalent group, a and a' represent 1 and 2, respectively; and b represents an integer of 1 to 20.

With regard to the fluorine-containing epoxy-modified organosilicon compound (A), specific examples of $Q^{11}$ in formula (1) include groups having the structures represented by the following formulas.

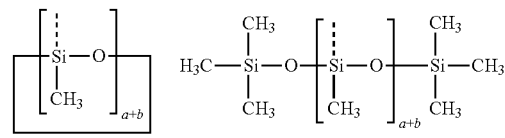

In the formulas, a and b are as defined above and are each preferably an integer of 1 to 4. Moreover, (a+b) is preferably an integer of 3 to 5. The unit repeated a times and the unit repeated b times are randomly arranged. The bond represented by the broken line in each of the unit repeated a times and the unit repeated b times is attached to $Rf^{11}$ or the group represented by the following formula:

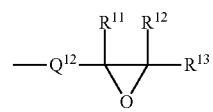

wherein $Q^{12}$ and $R^{11}$ to $R^{13}$ are as defined above.

The divalent hydrocarbon group for $Q^{12}$ in formula (1) preferably has 2 to 15 carbon atoms. Specific examples of the structure of $Q^{12}$ include —CH$_2$CH$_2$—, —CH$_2$CH(CH$_3$)—, and —CH$_2$CH$_2$CH$_2$OCH$_2$—.

The monovalent hydrocarbon group for $R^{11}$ to $R^{13}$ preferably has 1 to 8 carbon atoms. Specific examples of $R^{11}$ to $R^{13}$ include a hydrogen atom, alkyl groups such as methyl, ethyl, and propyl groups, and cycloalkyl groups such as cyclopentyl and cyclohexyl groups.

Examples of the group containing a combination of $R^{11}$ to $R^{13}$ and $Q^{12}$ represented by the above formula include the following groups.

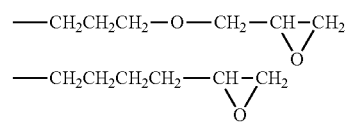

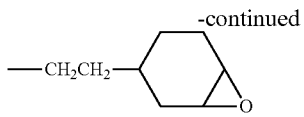

Rf$^{11}$ in formula (1) preferably has a molecular weight of 500 to 20,000. Moreover, Rf$^{11}$ may suitably contain 1 to 500, preferably 2 to 400, more preferably 4 to 200 repeating units of the formula: —C$_i$F$_{2i}$O— where i in each unit independently represents an integer of 1 to 6. In the present invention, the term "molecular weight" refers to a number average molecular weight calculated from the ratio between the chain end structure and the backbone structure as determined by $^1$H-NMR and $^{19}$F-NMR.

Examples of Rf$^{11}$ in formula (1) include groups represented by the following formula (3):

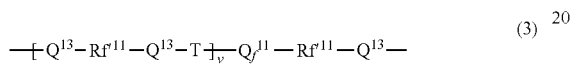

wherein Rf'$^{11}$ represents a divalent perfluoropolyether group having a molecular weight of 300 to 30,000 which may be internally branched; Q$^{13}$ represents a divalent organic group which may contain an oxygen atom, a nitrogen atom, a fluorine atom, or a silicon atom, and may contain a cyclic structure or an unsaturated bond; Q$_f^{11}$ represents Q$^{13}$ or a fluorine atom; T represents a linking group represented by the following formula (4):

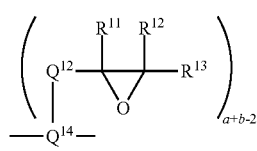

wherein R$^{11}$ to R$^{13}$, Q$^{12}$, a, and b are as defined in formula (1), and Q$^{14}$ represents an (a+b)-valent linking group containing at least (a+b) silicon atoms and having a siloxane structure, an unsubstituted or halogen-substituted silalkylene structure, a silarylene structure, or a combination of two or more thereof; and v represents an integer of 0 to 5, provided that v is 0 when Q$_f^{11}$ is a fluorine atom.

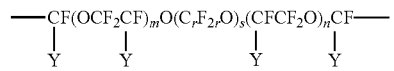

wherein each Y independently represents a fluorine atom or CF$_3$ group; r represents an integer of 2 to 6; m and n each represent an integer of 0 to 200, preferably 0 to 100, provided that (m+n) is an integer of 2 to 200, preferably 3 to 150; s represents an integer of 0 to 6; and the repeating units may be randomly linked, and

wherein j represents an integer of 1 to 3, and k represents an integer of 1 to 200, preferably 1 to 60.

Examples of Q$^{13}$ in formula (3) include the following groups:

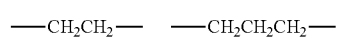

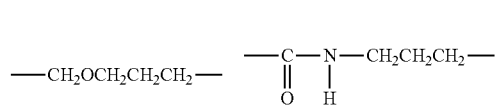

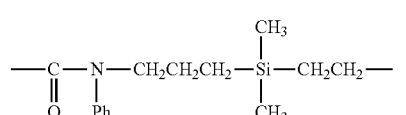

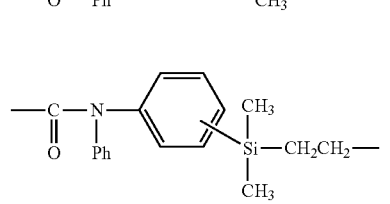

wherein Ph represents a phenyl group.

In formula (1), when Rf$^{11}$ is a monovalent group, a is preferably an integer of 1 to 3. The symbol b is preferably an integer of 1 to 6, and (a+b) is preferably an integer of 3 to 6.

Specific examples of Rf$^{12}$ in formula (1) include the following groups:

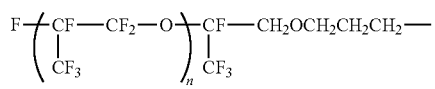

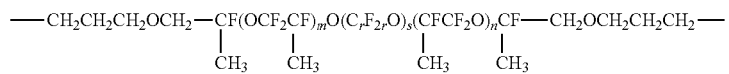

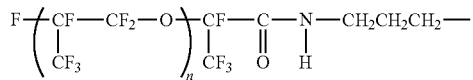

Rf$^{11}$ in formula (3) preferably has a molecular weight of 500 to 20,000. Specific examples of Rf$^{11}$ include divalent perfluoropolyether groups represented by the following formulas:

wherein m, n, r, and s are as defined above.

Specific examples of the fluorine-containing epoxy-modified organosilicon compound (A) include the following compounds:

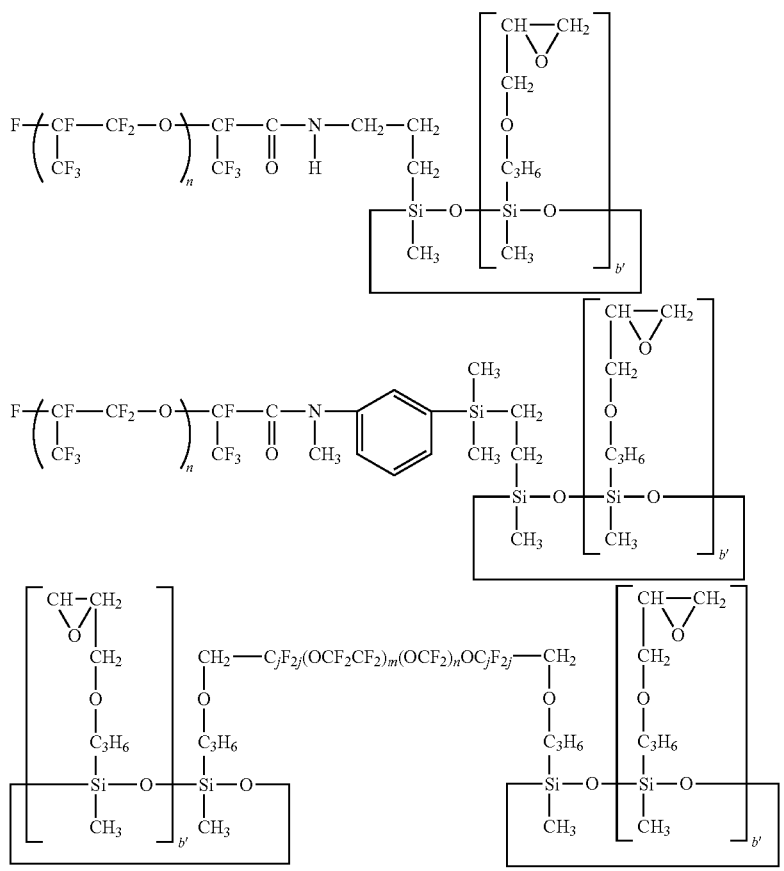

wherein j, m, and n are as defined above, and b' is an integer of 1 to 8.

These fluorine-containing epoxy-modified organosilicon compounds may be used alone or in combinations of two or more.

The unsaturated monocarboxylic acid (B) containing a (meth)acrylic group may suitably be acrylic acid or methacrylic acid although it may also be one in which a part of the hydrogen atoms is halogenated with a halogen atom (e.g. chlorine, fluorine), such as 2-chloroacrylic acid, 2-(trifluoromethyl)acrylic acid, or 2,3,3-trifluoroacrylic acid. These carboxylic acids may optionally be protected by an allyl group, a silyl group, or other groups. The unsaturated monocarboxylic acids may be used alone or in combinations of two or more.

The fluorine-containing (meth)acrylic-modified organosilicon compound may be produced by reacting the epoxy group of the fluorine-containing epoxy-modified organosilicon compound (A) with the carboxyl group of the unsaturated monocarboxylic acid (B) containing a (meth)acrylic group by a conventionally known method. Specific examples of the fluorine-containing (meth)acrylic-modified organosilicon compound include the following compounds:

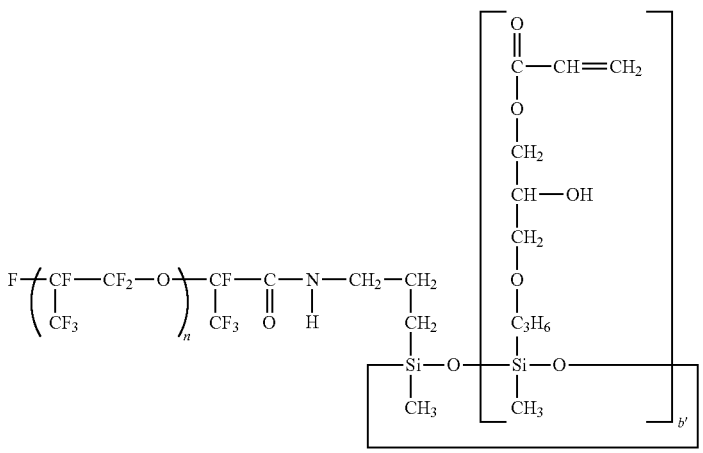

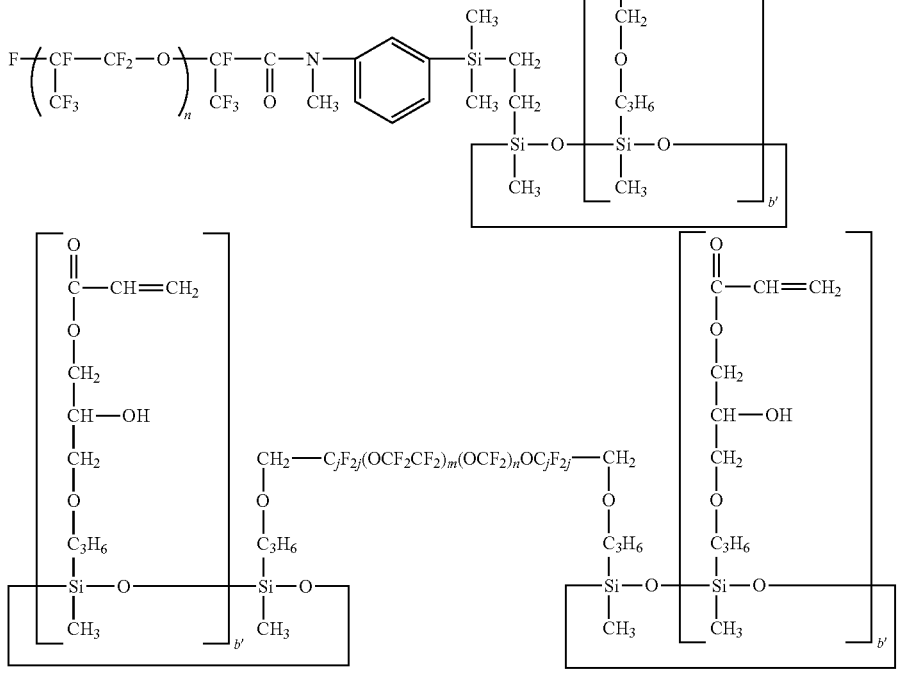

wherein j, m, n, and b' are as defined above.

The fluorine-containing monomer may suitably be a mixture of a fluorine-containing epoxy-modified organosilicon compound as specifically exemplified above and a fluorine-containing (meth)acrylic-modified organosilicon compound as specifically exemplified above. It is particularly preferably a mixture of a fluorine-containing epoxy-modified organosilicon compound and a fluorine-containing (meth)acrylic-modified organosilicon compound as represented by the formulas below:

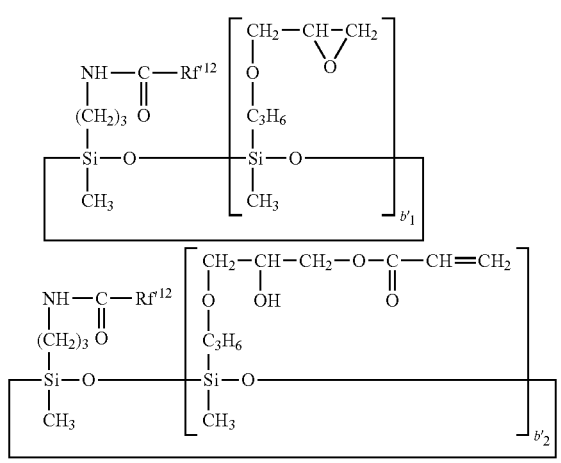

wherein $(b'_1+b'_2)$ is 2 to 6.5, and $Rf^{12}$ is a group represented by the following formula:

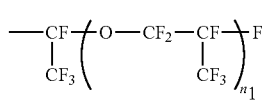

wherein $n_1$ is 2 to 100. In this case, the effects of the present invention can be better achieved.

The fluorine-containing monomer may also be a polyfunctional (meth)acrylate compound containing per molecule three or more fluorine atoms and three or more silicon atoms and having a cyclic siloxane represented by the following formula:

$(Rf^{21}R^{21}SiO)(R^4R^{21}SiO)_h$ wherein $R^{21}$ represents a hydrogen atom, a methyl group, an ethyl group, a propyl group, or a phenyl group; $Rf^{21}$ represents a fluorine-containing organic group; $R^A$ represents a (meth)acrylic group-containing organic group; and h satisfies h≥2.

$Rf^{21}$ in the polyfunctional (meth)acrylate compound may be a group represented by $C_tF_{2t+1}(CH_2)_u-$ where t represents an integer of 1 to 8, and u represents an integer of 2 to 10, or may be a perfluoropolyether-substituted alkyl group. Specific examples include $CF_3C_2H_4-$, $C_4F_9C_2H_4-$, $C_4F_9C_3H_6-$, $C_8F_{17}C_2H_4-$, $C_8F_{17}C_3H_6-$, $C_3F_7C(CF_3)_2C_3H_6-$, $C_3F_7OC(CF_3)$ FCF$_2$OCF$_2$CF$_2$C$_3$H$_6$—, C$_3$F$_7$OC(CF$_3$)FCF$_2$OC(CF$_3$)FC$_3$H$_6$—, and CF$_3$CF$_2$CF$_2$OC(CF$_3$)FCF$_2$OC(CF$_3$)FCONHC$_3$H$_6$—.

Specific examples of R$^4$ include CH$_2$=CHCOO—, CH$_2$=C(CH$_3$)COO—, CH$_2$=CHCOOC$_3$H$_6$—, CH$_2$=C(CH$_3$)COOC$_3$H$_6$—, CH$_2$=CHOOC$_2$H$_4$O—, and CH$_2$=C(CH$_3$)COOC$_2$H$_4$O—. Moreover, R$^4$ is preferably bonded to the silicon atom by a Si—O—C bond. The symbol h preferably satisfies 3≤h≤5.

The polyfunctional (meth)acrylate compound contains per molecule three or more fluorine atoms and three or more silicon atoms, and preferably contains per molecule 3 to 17 fluorine atoms and 3 to 8 silicon atoms.

Specific examples of the polyfunctional (meth)acrylate compound include compounds represented by the following formulas.

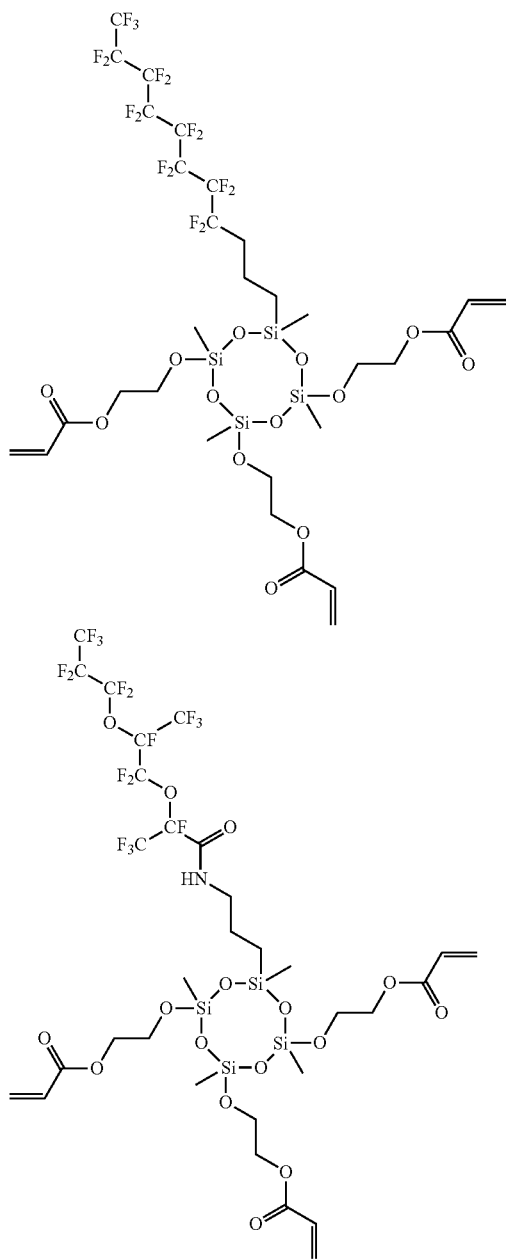

The fluorine-containing monomer is also preferably characterized by an infrared absorption spectrum having absorption peaks at about 1,045 cm$^{-1}$, about 1,180 cm$^{-1}$, about 806 cm$^{-1}$, about 1,720 cm$^{-1}$, about 1,532 cm$^{-1}$, and about 3,350 cm$^{-1}$. In particular, it may suitably be characterized by an infrared absorption spectrum having strong absorption peaks at about 1,045 cm$^{-1}$ and about 1,180 cm$^{-1}$, absorption peaks at about 806 cm$^{-1}$ and about 1,720 cm$^{-1}$, a weak absorption peak at about 1,532 cm$^{-1}$, and a broad weak absorption peak at about 3,350 cm$^{-1}$. In such a case, polymer chains having better properties including better sliding properties can be formed.

Moreover, the fluorine-containing monomer is preferably characterized by a $^{13}$C NMR spectrum in chloroform-d (deuterated chloroform) having signals at chemical shifts of about 13.01, 14.63, 23.04, 40.13, 50.65, 63.54, 68.97, 73.76, 76.74, 77.06, 77.38, 113.21, 114.11, 116.96, 117.72, 118.47, 128.06, 131.38, 156.46, and 166.02 ppm.

The fluorine-containing monomer is also preferably characterized by a $^1$H NMR spectrum in chloroform-d (deuterated chloroform) having signals at chemical shifts of about 3.40, 3.41, 3.49, 3.60, 5.26, 5.58, 6.12, 6.14, 6.40, 6.42, and 6.46 ppm.

In step 2, the monomer may be radically polymerized as follows. A solution of the monomer or the liquid monomer is applied (sprayed) to the surface of the gasket base material to which a benzophenone or thioxanthone compound or the like is adsorbed or covalently bonded. Alternatively, the gasket base material is immersed in a solution of the monomer or the liquid monomer. Then, the gasket base material is irradiated with light, such as ultraviolet light, to allow the radical polymerization (photoradical polymerization) to proceed, whereby polymer chains can be grown on the surface of the gasket base material. In another method, after the application, the surface may be covered with a transparent cover of glass, PET, polycarbonate or other materials, followed by irradiating the covered surface with light, such as ultraviolet light, to allow the radical polymerization (photoradical polymerization) to proceed, whereby polymer chains can be grown on the surface of the gasket base material.

The amount of the radically polymerizable monomer used may be chosen appropriately depending on, for example, the length of polymer chains to be formed, or the properties to be provided by the chains.

The solvent for application (spraying), the method for application (spraying), the method for immersion, the conditions for irradiation, and other conditions may be conventionally known materials or methods. The solution of the radically polymerizable monomer may be an aqueous solution, or a solution in an organic solvent that does not dissolve the photopolymerization initiator used (e.g. benzophenone or thioxanthone compound). Furthermore, a solution of the radically polymerizable monomer or the liquid radically polymerizable monomer may contain a known polymerization inhibitor such as 4-methylphenol.

The radical polymerization of the monomer is allowed to proceed by light irradiation after the application of a solution of the monomer or the liquid monomer or after the immersion in a solution of the monomer or the liquid monomer. Here, UV light sources with an emission wavelength mainly in the ultraviolet region, such as high-pressure mercury lamps, metal halide lamps, and LED lamps, can be suitably used. The light dose may be appropriately selected in view of polymerization time and uniform reaction progress. In order to prevent inhibition of polymerization due to active gas such as oxygen in the reaction vessel, oxygen is preferably removed from the reaction vessel and the reaction solution during or before the light irradiation. To this end, appropriate operations may be performed. For example, an inert gas such as nitrogen gas or argon gas is inserted into the reaction vessel and the reaction solution to discharge active gas such as oxygen from the reaction system and thereby replace the atmosphere in the reaction system with the inert gas. Or the reaction vessel is evacuated to remove oxygen. Also, in order to prevent inhibition of the reaction due to oxygen and other gases, a measure may appropriately be taken; for example, an UV light source is placed such that an air layer (oxygen content: 15% or higher) does not exist between the reaction vessel made of glass, plastic, or other materials and the reaction solution or the gasket base material.

In the case of irradiation with ultraviolet light, the ultraviolet light preferably has a wavelength of 300 to 450 nm, more preferably 300 to 400 nm. Such light allows polymer chains to be formed well on the surface of the gasket base material. The light source may be, for example, a high-pressure mercury lamp, an LED with a center wavelength of 365 nm, or an LED with a center wavelength of 375 nm. In particular, preferred is irradiation with LED light having a wavelength of 300 to 450 nm, more preferably 355 to 380 nm. In particular, LEDs or other light sources having a center wavelength of 365 nm, which is close to the excitation wavelength (366 nm) of benzophenone, are preferred in view of efficiency.

The surface modification method may include (i) step 3 of extending each polymer chain grown in step 2 by adding the same or a different polymer chain, or (ii) step 3' of attaching a silane compound to the surface of each polymer chain grown in step 2, followed by reaction with a perfluoroether group-containing silane compound to grow a functional polymer chain.

Step 3 is not particularly limited as long as it involves further extending the polymer chain. For example, step 3 may include step 3-1 of forming polymerization initiation points B on the surface of each polymer chain grown in step 2, and step 3-2 of radically polymerizing a monomer starting from the polymerization initiation points B to grow polymer chains.

In step 3-1, the formation of polymerization initiation points B may be carried out by the same techniques as mentioned in step 1, such as by additionally adsorbing a photopolymerization initiator B onto the surface of the formed polymer chains, optionally followed by chemically bonding the photopolymerization initiator B to the surface. The photopolymerization initiator B may be as described for the photopolymerization initiator A.

In step 3-2, a monomer is radically polymerized starting from the polymerization initiation points B to grow polymer chains.

The monomer used in step 3-2 may be as described for the monomer used in step 2. In particular, the monomer is preferably (meth)acrylonitrile or a fluorine-containing monomer, more preferably a fluorine-containing monomer, because they provide excellent resistance to liquid leakage and excellent sliding properties.

In step 3-2, the monomer may be radically polymerized as mentioned for the radical polymerization in step 2.

In step 3, the cycle of steps 3-1 and 3-2 may further be repeated. In this case, the polymer chain that has been chain extended in steps 3-1 and 3-2 is extended by addition of a polymer chain.

In step 3', on the other hand, a silane compound is attached to the surface of each polymer chain formed in step 2, and then reacted with a perfluoroether group-containing silane compound to grow a functional polymer chain (functional moiety).

The silane compound is not particularly limited, and suitable examples include alkoxysilanes and modified alkoxysilanes. These compounds may be used alone or in combinations of two or more. Among these, alkoxysilanes are more preferred in order to better achieve the effects of the present invention.

Examples of alkoxysilanes include: monoalkoxysilanes such as trimethylmethoxysilane, triethylethoxysilane, tripropylpropoxysilane, and tributylbutoxysilane; dialkoxysilanes such as dimethyldimethoxysilane, diethyldiethoxysilane, dipropyldipropoxysilane, and dibutyldibutoxysilane; trialkoxysilanes such as methyltrimethoxysilane, ethyltriethoxysilane, propyltripropoxysilane, and butyltributoxysilane; and tetraalkoxysilanes such as tetramethoxysilane, tetraethoxysilane, tetrapropoxysilane, tetrabutoxysilane, dibutoxydiethoxysilane, butoxytriethoxysilane, and ethoxytriethoxysilane. These compounds may be used alone or in combinations of two or more. In order to better achieve the effects of the present invention, tetraalkoxysilanes are preferred among these, with tetramethoxysilane, tetraethoxysilane, tetrabutoxysilane, dibutoxydiethoxysilane, butoxytriethoxysilane, and ethoxytributoxysilane being more preferred.

The term "modified alkoxysilane" refers to an alkoxysilane having a substituent such as an amino, carboxyl, hydroxy, or epoxy group, and preferably contains at least one substituent selected from the group consisting of alkyl, amino, carboxyl, hydroxy, and epoxy groups.

In order to better achieve the effects of the present invention, the alkoxysilane or modified alkoxysilane preferably has 4 to 22 carbon atoms, more preferably 4 to 16 carbon atoms.

In order to better achieve the effects of the present invention, the alkoxysilane or modified alkoxysilane preferably contains at least one selected from the group consisting of methoxy, ethoxy, propoxy, and butoxy groups, more preferably an ethoxy group and/or a butoxy group, still more preferably an ethoxy group and a butoxy group.

Examples of commercial products of the silane compound include Primer coat PC-3B (Fluoro Technology, a butoxy/ethoxy tetraalkoxysilane represented by the following formula).

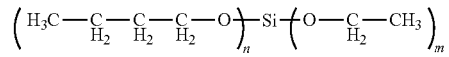

In the formula, m+n=4 with n>m>0 on average.

In step 3', the silane compound may be attached to the surface of the polymer chain by any method, and conventional methods may appropriately be used, such as bringing the silane compound into contact with the object to be modified on which polymer chains are formed.

The perfluoroether group-containing silane compound may be any silane compound containing a perfluoroether group. For example, it may suitably be a compound represented by the following formula (A) or (B):

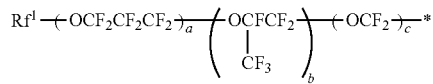

-continued

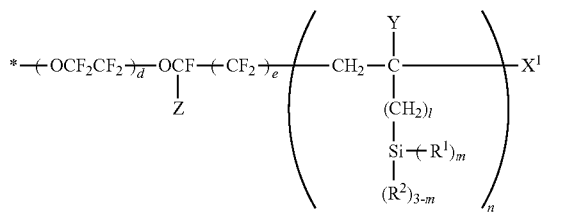
(A)

wherein $Rf^1$ represents a perfluoroalkyl group; Z represents fluorine or a trifluoromethyl group; a, b, c, d, and e are the same as or different from one another and each represent an integer of 0 or 1 or more, provided that (a+b+c+d+e) is 1 or more and the order of the repeating units parenthesized by subscripts a, b, c, d, and e occurring in the formula is not limited to that shown; Y represents hydrogen or a C1-C4 alkyl group; $X^1$ represents hydrogen, bromine, or iodine; $R^1$ represents a hydroxy group or a hydrolyzable substituent such as a C1-C4 alkoxy group; $R^2$ represents hydrogen or a monovalent hydrocarbon group; l represents 0, 1, or 2; m represents 1, 2, or 3; and n represents an integer of 1 or more, provided that the two ends marked by * are directly bonded to each other,

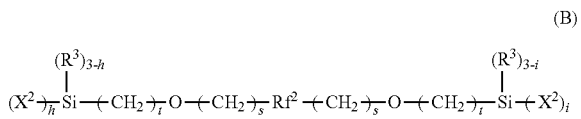
(B)

wherein $Rf^2$ represents a divalent group having a non-branched linear perfluoropolyalkylene ether structure that contains a unit represented by —$(C_kF_{2k})O$— where k is an integer of 1 to 6; each $R^3$ is the same or different and represents a C1-C8 monovalent hydrocarbon group; each $X^2$ is the same or different and represents a hydrolyzable group such as a C1-C4 alkoxy group, or a halogen atom; each s is the same or different and represents an integer of 0 to 2; each t is the same or different and represents an integer of 1 to 5; and h and i are the same as or different from each other and each represent 1, 2, or 3.

$Rf^1$ in formula (A) may be any perfluoroalkyl group that can be present in a common organic-containing fluoropolymer, and examples include linear or branched C1-C16 groups. Preferred are $CF_3$—, $C_2F_5$—, and $C_3F_7$—, among others.

In formula (A), each of a, b, c, d, and e represents the number of repeating units in the perfluoropolyether chain which forms the backbone of the fluorine-containing silane compound, and is independently preferably 0 to 200, more preferably 0 to 50. Moreover, (a+b+c+d+e), i.e. the sum of a to e, is preferably 1 to 100. The order of the repeating units parenthesized by subscripts a, b, c, d, and e occurring in formula (A) is not limited to the order shown, and the repeating units may be joined in any order.

Examples of the C1-C4 alkyl group represented by Y in formula (A) include methyl, ethyl, propyl, and butyl groups, and the alkyl group may be linear or branched. When $X^1$ is bromine or iodine, the fluorine-containing silane compound easily forms a chemical bond.

The hydrolyzable substituent represented by $R^1$ in formula (A) is not particularly limited. Preferred examples include halogens, —$OR^4$, —$OCOR^4$, —$OC(R^4)=C(R^5)_2$, —$ON=C(R^4)_2$, and —$ON=CR^6$, where $R^4$ represents an aliphatic hydrocarbon group or an aromatic hydrocarbon group; $R^5$ represents hydrogen or a C1-C4 aliphatic hydrocarbon group; and $R^6$ represents a divalent C3-C6 aliphatic hydrocarbon group. More preferred are chlorine, —$OCH_3$, and —$OC_2H_5$. The monovalent hydrocarbon group represented by $R^2$ is not particularly limited, and preferred examples include methyl, ethyl, propyl, and butyl groups. The hydrocarbon group may be linear or branched.

In formula (A), l represents the number of carbon atoms of the alkylene group between the carbon in the perfluoropolyether chain and the silicon attached thereto and is preferably 0; and m represents the number of substituents $R^1$ bonded to the silicon to which $R^2$ is bonded through a bond not attached to $R^1$. The upper limit of n is not particularly limited and is preferably an integer of 1 to 10.

In formula (B), on the other hand, the group represented by $Rf^2$ is preferably, but not limited to, such that when each s is 0, the ends of the $Rf^2$ group bonded to oxygen atoms in formula (B) are not oxygen atoms. Moreover, k in $Rf^2$ is preferably an integer of 1 to 4. Specific examples of the group represented by $Rf^2$ include —$CF_2CF_2O(CF_2CF_2CF_2O)_jCF_2CF_2$— in which j represents an integer of 1 or more, preferably of 1 to 50, more preferably of 10 to 40; and —$CF_2(OC_2F_4)_p$—$(OCF_2)_q$— in which p and q each represent an integer of 1 or more, preferably of 1 to 50, more preferably of 10 to 40, and the sum of p and q is an integer of 10 to 100, preferably of 20 to 90, more preferably of 40 to 80, and the repeating units ($OC_2F_4$) and ($OCF_2$) are randomly arranged.

$R^3$ in formula (B) is preferably a C1-C30 monovalent hydrocarbon group, and examples include: alkyl groups such as methyl, ethyl, propyl, butyl, pentyl, hexyl, heptyl, and octyl groups; cycloalkyl groups such as cyclopentyl and cyclohexyl groups; aryl groups such as phenyl, tolyl, and xylyl groups; aralkyl groups such as benzyl and phenethyl groups; and alkenyl groups such as vinyl, allyl, butenyl, pentenyl, and hexenyl groups. Preferred among these is a methyl group.

Examples of the hydrolyzable group represented by $X^2$ in formula (B) include: alkoxy groups such as methoxy, ethoxy, propoxy, and butoxy groups; alkoxyalkoxy groups such as methoxymethoxy, methoxyethoxy, and ethoxyethoxy groups; alkenyloxy groups such as allyloxy and isopropenoxy groups; acyloxy groups such as acetoxy, propionyloxy, butylcarbonyloxy, and benzoyloxy groups; ketoxime groups such as dimethylketoxime, methylethylketoxime, diethylketoxime, cyclopennoxime, and cyclohexanoxime groups; amino groups such as N-methylamino, N-ethylamino, N-propylamino, N-butylamino, N,N-dimethylamino, N,N-diethylamino, and N-cyclohexylamino groups; amide groups such as N-methylacetamide, N-ethylacetamide, and N-methylbenzamide groups; and aminooxy groups such as N,N-dimethylaminooxy and N,N-diethylaminooxy groups. Examples of the halogen atom represented by $X^2$ include chlorine, bromine, and iodine atoms. Preferred among these are a methoxy group, an ethoxy group, an isopropenoxy group, and a chlorine atom.

In formula (B), s is preferably 1, while t is preferably 3. In view of hydrolyzability, h and i are each preferably 3.

For durable mold-releasing effect, the perfluoroether group-containing silane compound preferably has an average molecular weight in the range of 1,000 to 10,000. The average molecular weight can be determined by gel permeation chromatography (GPC) calibrated with polystyrene standards.

Examples of commercial products of the perfluoroether group-containing silane compound include OPTOOL DSX (Daikin Industries, Ltd.), KY-108 and KY-164 (Shin-Etsu Chemical Co., Ltd.), Fluorolink S10 (Solvay Specialty Polymers Japan K.K.), Novec 2702 and Novec 1720 (3M Japan Limited), and FLUOROSURF series such as FLUOROSURF FG-5080SH (Fluoro Technology).

In step 3', the reaction with the perfluoroether group-containing silane compound after the attachment of the silane compound may be carried out by any method, and conventional methods may appropriately be used, such as bringing a solution of the perfluoroether group-containing silane compound into contact with the object to be modified to which the silane compound is attached. The solution of the perfluoroether group-containing silane compound may be prepared by using a known solvent that can dissolve the compound (e.g. water, perfluorohexane, acidic water, methanol, ethanol, or a mixture of water and methanol or ethanol), followed by appropriately adjusting the concentration. The contact between the solution and the object may be made by any method that brings them into contact with each other, such as application, spraying, or immersion.

In the reaction with the perfluoroether group-containing silane compound, the contact (e.g. immersion) is preferably followed by maintenance at a humidity of 50% or higher. This promotes the reaction so that the effects of the present invention can be well achieved. The humidity is more preferably 60% or higher, still more preferably 80% or higher. The upper limit of the humidity is not particularly limited but is preferably, for example, 100% or lower. The maintenance time and temperature may be appropriately selected and are preferably, for example, 0.5 to 60 hours and 20 to 100° C., respectively.

The gasket of the present invention may also be prepared by immobilizing polymer chains by a surface modification method that includes step I of radically polymerizing a monomer in the presence of a photopolymerization initiator A on the surface of a gasket base material to grow polymer chains.

For example, step I may be carried out by bringing a photopolymerization initiator A and a monomer into contact with the surface of a gasket base material, followed by irradiation with LED light having a wavelength of 300 to 450 nm to form polymerization initiation points A from the photopolymerization initiator A while radically polymerizing the monomer starting from the polymerization initiation points A to grow polymer chains.

The surface modification method including step I may include (i) step II of extending each polymer chain grown in step I by adding the same or a different polymer chain; or (ii) step II' of attaching a silane compound to the surface of each polymer chain grown in step I, followed by reaction with a perfluoroether group-containing silane compound to grow a functional polymer chain.

Step II may be carried out by bringing a photopolymerization initiator B and a monomer into contact with the surface of each polymer chain formed in step I, followed by irradiation with LED light having a wavelength of 300 to 450 nm to form polymerization initiation points B from the photopolymerization initiator B while radically polymerizing the monomer starting from the polymerization initiation points B to grow polymer chains. The extension process may be repeated in step II. In this case, the polymer chain that has been chain-extended is further extended.

In steps I and II, the monomers may be radically polymerized as follows. A solution of the monomer or the liquid monomer, which contains the photopolymerization initiator A or B (e.g. benzophenone or thioxanthone compound), is applied (sprayed) to the surface of a gasket base material or the gasket base material on which polymer chains are formed in step I. Alternatively, a gasket base material or the gasket base material on which polymer chains are formed in step I is immersed in a solution of the monomer or the liquid monomer, which contains the photopolymerization initiator A or B. Then, the gasket base material is irradiated with light, such as ultraviolet light, to allow the radical polymerization (photoradical polymerization) to proceed, whereby polymer chains can be grown or extended on the surface of the gasket base material. In another method, for example, the surface may be covered with a transparent cover of glass, PET, polycarbonate or other materials, followed by irradiating the covered surface with light such as ultraviolet light, as described above. Here, a reducing agent or an antioxidant may be added. The solvent for application (spraying), the method for application (spraying), the method for immersion, the conditions for irradiation, and other conditions may be materials or methods as mentioned above.

In step II', on the other hand, a silane compound is attached to the surface of each polymer chain grown in step I, and then reacted with a perfluoroether group-containing silane compound to grow a functional polymer chain (functional moiety). Step II' may be carried out as described in step 3'.

The polymer chains finally formed by the surface modification method preferably have a polymerization degree of 20 to 200,000, more preferably 350 to 50,000.

The total length of the finally formed polymer chain is preferably 10 to 50,000 nm, more preferably 100 to 50,000 nm, still more preferably 500 to 10,000 nm. When the total length is shorter than 10 nm, good sliding properties tend not to be obtained. When the total length is longer than 50,000 nm, a further improvement in sliding properties cannot be expected while the cost of raw materials tends to increase due to the use of the expensive monomer. In addition, surface patterns generated by the surface treatment tend to be visible to the naked eyes, thereby spoiling the appearance and deteriorating sealing properties.

In the above-described polymerization processes, two or more types of monomers may simultaneously be radically polymerized starting from the polymerization initiation points A or B. Moreover, multiple types of polymer chains may be grown on the surface of the gasket base material. In the surface modification method, the polymer chains may be crosslinked to one another. In this case, the polymer chains may be crosslinked to one another by ionic crosslinking, crosslinking by a hydrophilic group containing an oxygen atom, or crosslinking by a halogen group such as iodine. Crosslinking by UV irradiation or electron beam irradiation may also be employed.

The surface of the gasket base material may be at least partially or entirely provided with polymer chains.

In particular, in view of sliding properties and other properties, preferably at least the sliding surface of the gasket base material is modified.

EXAMPLES

Examples 1 to 14

A gasket base material (an isoprene unit-containing chlorobutyl rubber (degree of unsaturation: 1 to 2%) crosslinked by triazine (vulcanized at 180° C. for 10 minutes)) having the shape indicated in Table 1 (FIG. 1, three annular projections (first projection, intermediate projection, and bottom projection) and two annular valleys) was immersed in a 3 wt % solution of benzophenone in acetone for 5 minutes so that benzophenone was adsorbed onto the surface of the gasket base material, followed by drying.

The dried gasket base material was immersed in a 2.5 M acrylamide aqueous solution in a glass reaction vessel, and then irradiated with LED-UV light having a wavelength of 365 nm for 150 minutes to cause radical polymerization, whereby polymer chains were grown on the rubber surface. In this manner, a desired gasket was prepared.

Example 15

A gasket base material (an isoprene unit-containing chlorobutyl rubber (degree of unsaturation: 1 to 2%) crosslinked by triazine (vulcanized at 180° C. for 10 minutes)) having the shape indicated in Table 1 (FIG. 1, three annular projections (first projection, intermediate projection, and bottom projection) and two annular valleys) was immersed in a 3 wt % solution of benzophenone in acetone so that benzophenone was adsorbed onto the surface of the gasket base material, followed by drying.

The dried gasket base material was immersed in a 2.5 M aqueous mixture of acrylamide and acrylic acid (acrylamide:acrylic acid=75:25) in a glass reaction vessel, and then irradiated with LED-UV light having a wavelength of 365 nm for 90 minutes to cause radical polymerization, whereby polymer chains were grown on the rubber surface. Thereafter, the surface was washed with water and dried.

Next, the dried gasket was again immersed in a 3 wt % solution of benzophenone in acetone for 5 minutes so that benzophenone was adsorbed onto the surface of the polymer chains, followed by drying.

Further, a fluorine-containing monomer liquid (a 20 wt % dilution in ethanol of KY-1203 available from Shin-Etsu Chemical Co., Ltd. (a mixture of a fluorine-containing epoxy-modified organosilicon compound and a fluorine-containing (meth)acrylic-modified organosilicon compound as represented by the formulas below)) was applied to the surface of the dried gasket, followed by irradiation with LED-UV light having a wavelength of 365 nm for 10 minutes to cause radical polymerization, whereby the polymer chains were extended. In this manner, a desired gasket was prepared.

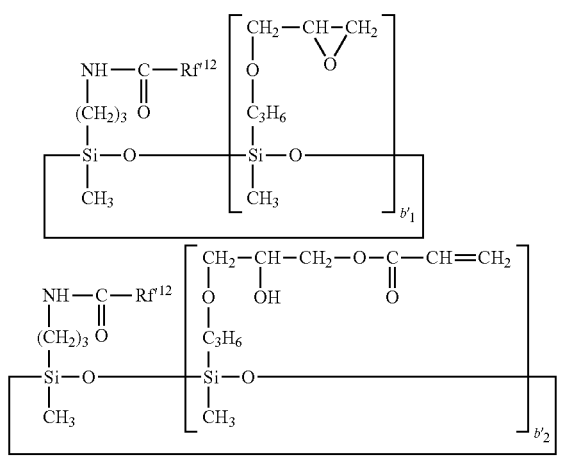

In the formulas, $(b'_1+b'_2)$ is 2 to 6.5, and $Rf^{12}$ is the following group:

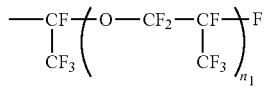

wherein $n_1$ is 2 to 100.

Examples 16 and 17

A gasket base material (a vulcanized rubber gasket (vulcanized at 180° C. for 10 minutes) prepared by crosslinking an isoprene unit-containing chlorobutyl rubber (degree of unsaturation: 1 to 2%) by triazine) having the shape indicated in Table 1 (FIG. 1, three annular projections (first projection, intermediate projection, and bottom projection) and two annular valleys) was immersed in a 2.5 M aqueous mixture of acrylic acid and acrylamide (25:75, prepared by dissolving 4.5 g of acrylic acid and 13.4 g of acrylamide in 100 mL of water and then dissolving 2 mg of benzophenone in the solution) in a glass reaction vessel, followed by irradiation with LED-UV light having a wavelength of 365 nm for 40 minutes to cause radical polymerization, whereby non-functional polymer chains were grown on the rubber surface. Thereafter, the surface was washed with water and dried.

Next, the dried vulcanized rubber gasket was immersed in Primer coat PC-3B (a silane compound, Fluoro Technology), taken out, and dried.

Then, the dried vulcanized rubber gasket was immersed in a 2% solution of a perfluoroether group-containing silane compound (OPTOOL DSX-E available from Daikin Industries, Ltd., a compound of formula (A)) in $C_4F_9OC_2H_5$ (Novec HFE-7200 available from 3M), and taken out of the solution. The resulting gasket was left to stand at a humidity of 90% for 24 hours to cause a reaction. Thereafter, the gasket was washed with acetone and dried. In this manner, a surface-modified elastic body (polymer brush) was produced.

Comparative Example 1

A vulcanized rubber gasket (vulcanized at 180° C. for 10 minutes) prepared by crosslinking an isoprene unit-containing chlorobutyl rubber (degree of unsaturation: 1 to 2%) by triazine, was used as it was.

Comparative Examples 2 to 5

A gasket base material (an isoprene unit-containing chlorobutyl rubber (degree of unsaturation: 1 to 2%) crosslinked by triazine (vulcanized at 180° C. for 10 minutes)) having the shape indicated in Table 1 (FIG. 1, three annular projections (first projection, intermediate projection, and bottom projection) and two annular valleys) was immersed in a 3 wt % solution of benzophenone in acetone for 5 minutes so that benzophenone was adsorbed onto the surface of the gasket base material, followed by drying.

The dried gasket base material was immersed in a 2.5 M acrylamide aqueous solution in a glass reaction vessel, and then irradiated with LED-UV light having a wavelength of 365 nm for 150 minutes to cause radical polymerization, whereby polymer chains were grown on the rubber surface. In this manner, a desired gasket was prepared.

The surface-modified elastic bodies prepared in the examples and comparative examples were evaluated as follows.

(Polymer Chain Length)

To determine the total length of the polymer chain formed on the surface of the gasket, a cross-section of the gasket with polymer chains formed thereon was analyzed with an SEM at an accelerating voltage of 15 kV and a magnification of 1,000 times. The thickness of the polymer layer photographed was taken as the polymer chain length.

(Sliding Properties (Friction Resistance))

To determine the friction resistance of the surface of the gasket, the vulcanized rubber gasket prepared in each of the examples and comparative examples was inserted into a COP resin barrel of a syringe and then pushed towards the end of the barrel (push rate: 30 mm/min) using a tensile tester while friction resistance was measured. The friction resistances of the examples are expressed as a friction resistance index using the equation below, with Comparative Example 1 set equal to 100. A lower index indicates a lower friction resistance.

(Friction resistance index)=(Friction resistance of each example)/(Friction resistance of Comparative Example 1)×100

(Resistance to Liquid Leakage)

The vulcanized rubber gasket prepared in each of the examples and comparative examples was inserted into a COP resin barrel of a syringe. A solution of red food coloring in water was introduced into the barrel, and the barrel was sealed with a cap. After two week storage at 40° C., the barrel was visually observed for liquid leakage.

TABLE 1

| | Outer diameter of first projection (mm) | Outer diameter of intermediate projection (mm) | Ratio of outer diameter of intermediate projection to outer diameter of first projection (%) | Outer diameter of bottom projection (mm) | Ratio of outer diameter of bottom projection to outer diameter of first projection (%) | Outer diameter of (two) annular valleys (mm) | Ratio of outer diameter of annular valley to outer diameter of first projection (%) | Annular flat portion of first projection (mm) |
|---|---|---|---|---|---|---|---|---|
| Ex. 1 | 6.70 | 6.45 | 96.3 | 6.45 | 96.3 | 5.90 | 88.1 | 0.20 |
| Ex. 2 | 6.80 | 6.45 | 94.9 | 6.45 | 94.9 | 6.00 | 88.2 | 0.20 |
| Ex. 3 | 6.60 | 6.45 | 97.7 | 6.45 | 97.7 | 5.80 | 87.9 | 0.20 |
| Ex. 4 | 6.70 | 6.45 | 96.3 | 6.45 | 96.3 | 6.10 | 91.0 | 0.20 |
| Ex. 5 | 6.70 | 6.45 | 96.3 | 6.45 | 96.3 | 5.75 | 85.8 | 0.20 |
| Ex. 6 | 6.70 | 6.40 | 95.5 | 6.45 | 96.3 | 5.90 | 88.1 | 0.20 |
| Ex. 7 | 6.70 | 6.45 | 96.3 | 6.45 | 96.3 | 5.90 | 88.1 | 0.20 |
| Ex. 8 | 6.70 | 6.45 | 96.3 | 6.45 | 96.3 | 5.90 | 88.1 | 0.20 |
| Ex. 9 | 6.70 | 6.45 | 96.3 | 6.45 | 96.3 | 5.90 | 88.1 | 0.20 |
| Ex. 10 | 6.70 | 6.45 | 96.3 | 6.45 | 96.3 | 5.90 | 88.1 | 0.20 |
| Ex. 11 | 6.70 | 6.45 | 96.3 | 6.45 | 96.3 | 5.90 | 88.1 | 0.20 |
| Ex. 12 | 6.70 | 6.45 | 96.3 | 6.45 | 96.3 | 5.90 | 88.1 | 0.20 |
| Ex. 13 | 6.70 | 6.45 | 96.3 | 6.45 | 96.3 | 5.90 | 88.1 | 0.10 |
| Ex. 14 | 6.70 | 6.45 | 96.3 | 6.45 | 96.3 | 5.90 | 88.1 | 0.25 |
| Ex. 15 | 6.70 | 6.45 | 96.3 | 6.45 | 96.3 | 5.90 | 88.1 | 0.20 |
| Ex. 16 | 6.70 | 6.45 | 96.3 | 6.45 | 96.3 | 5.90 | 88.1 | 0.20 |
| Ex. 17 | 6.70 | 6.45 | 96.3 | 6.45 | 96.3 | 5.90 | 88.1 | 0.20 |
| Com. Ex. 1 | 6.80 | 6.45 | 94.9 | 6.45 | 94.9 | 5.90 | 86.8 | 0.20 |
| Com. Ex. 2 | 6.80 | 6.37 | 93.7 | 6.37 | 93.7 | 5.90 | 86.8 | 0.20 |
| Com. Ex. 3 | 6.80 | 6.70 | 98.5 | 6.70 | 98.5 | 5.90 | 86.8 | 0.20 |
| Com. Ex. 4 | 6.70 | 6.45 | 96.3 | 6.45 | 96.3 | 5.60 | 83.6 | 0.20 |
| Com. Ex. 5 | 6.70 | 6.45 | 96.3 | 6.45 | 96.3 | 6.20 | 92.5 | 0.20 |

| | Curvature of first projection on top side | Curvature of first projection on bottom side | Curvature of intermediate projection/ bottom projection on top and bottom sides | Curvature of (two) annular valleys | Monomer used in first layer | Monomer used in second layer | Total polymer chain length (nm) | Sliding properties | Resistance to liquid leakage |
|---|---|---|---|---|---|---|---|---|---|
| Ex. 1 | 0.3 | 0.3 | 0.3 | 0.3 | Acrylamide | None | 5000 | 2.5 | Pass |
| Ex. 2 | 0.3 | 0.3 | 0.3 | 0.3 | Acrylamide | None | 5000 | 3.0 | Pass |
| Ex. 3 | 0.3 | 0.3 | 0.3 | 0.3 | Acrylamide | None | 5000 | 2.2 | Pass |
| Ex. 4 | 0.3 | 0.3 | 0.3 | 0.3 | Acrylamide | None | 5000 | 2.3 | Pass |
| Ex. 5 | 0.3 | 0.3 | 0.3 | 0.3 | Acrylamide | None | 5000 | 3.0 | Pass |
| Ex. 6 | 0.3 | 0.3 | 0.3 | 0.3 | Acrylamide | None | 5000 | 2.3 | Pass |
| Ex. 7 | 0.3 | 0.6 | 0.3 | 0.3 | Acrylamide | None | 5000 | 2.2 | Pass |
| Ex. 8 | 0.1 | 0.3 | 0.3 | 0.3 | Acrylamide | None | 5000 | 3.0 | Pass |
| Ex. 9 | 0.3 | 0.3 | 0.6 | 0.3 | Acrylamide | None | 5000 | 2.2 | Pass |
| Ex. 10 | 0.3 | 0.3 | 0.3 | 0.6 | Acrylamide | None | 5000 | 2.2 | Pass |
| Ex. 11 | 0.3 | 0.3 | 0.3 | 1 | Acrylamide | None | 5000 | 2.0 | Pass |
| Ex. 12 | 0.3 | 0.3 | 0.6 | 1.5 | Acrylamide | None | 5000 | 1.8 | Pass |
| Ex. 13 | 0.3 | 0.3 | 0.3 | 0.3 | Acrylamide | None | 5000 | 2.1 | Pass |
| Ex. 14 | 0.3 | 0.3 | 0.3 | 0.3 | Acrylamide | None | 5000 | 2.8 | Pass |
| Ex. 15 | 0.3 | 0.3 | 0.3 | 0.3 | Acrylamide/ Acrylic acid | KY1203 | 2500 | 2.0 | Pass |

TABLE 1-continued

| | | | | | | | | | |
|---|---|---|---|---|---|---|---|---|---|
| Ex. 16 | 0.3 | 0.3 | 0.3 | 0.3 | Acrylamide/ Acrylic acid | Primer coat + DSX-E | 1000 | 1.6 | Pass |
| Ex. 17 | 0.3 | 0.3 | 0.6 | 1 | Acrylamide/ Acrylic acid | Primer coat + DSX-E | 1000 | 1.4 | Pass |
| Com. Ex. 1 | 0.3 | 0.3 | 0.3 | 0.3 | No graft polymer | — | 0 | 100 | Pass |
| Com. Ex. 2 | 0.3 | 0.3 | 0.3 | 0.3 | Acrylamide | None | 5000 | 2.2 | Fail |
| Com. Ex. 3 | 0.3 | 0.3 | 0.3 | 0.3 | Acrylamide | None | 5000 | 5.2 | Pass |
| Com. Ex. 4 | 0.3 | 0.3 | 0.3 | 0.3 | Acrylamide | None | 5000 | 2.8 | Fail |
| Com. Ex. 5 | 0.3 | 0.3 | 0.3 | 0.3 | Acrylamide | None | 5000 | 3.6 | Pass |

Table 1 demonstrates that the surfaces of the gaskets of the examples exhibited greatly reduced friction resistance and thus had good sliding properties.

In contrast, the gasket of Comparative Example 2 with intermediate and bottom projections having a small outer diameter tended to be bent when it was inserted into a barrel because the projections failed to act sufficiently as guides. For this reason, its top projection was more likely to be askew so that a gap occurred, resulting in liquid leakage. The gasket of Comparative Example 3 with intermediate and bottom projections having a large outer diameter exhibited inferior sliding properties with a friction resistance index of 3.5 or higher.

The gasket of Comparative Example 4 with an annular valley having a small outer diameter tended to be bent when it was inserted into a barrel because it had high projections. For this reason, its first projection was more likely to be askew so that a gap occurred, resulting in liquid leakage. The gasket of Comparative Example 5 with an annular valley having a large outer diameter exhibited inferior sliding properties with a friction resistance index of 3.5 or higher.

Thus, when the gasket of the present invention is used as a gasket of a syringe plunger, it is possible to provide sufficient resistance to liquid leakage while reducing the friction of the plunger against the syringe barrel, and therefore to provide an easy and accurate treatment with the syringe. Moreover, the gasket has a small difference between static and kinetic coefficients of friction, and therefore the start of pushing the plunger and the subsequent inward movement of the plunger can be smoothly carried out without pulsation. Furthermore, when polymer chains are formed on the inner surface of a syringe barrel made of a thermoplastic elastomer, the treatment with the syringe can be facilitated as described above.

REFERENCE SIGNS LIST

1: gasket base material
12: top surface
13: bottom surface
14: sliding portion
14a: first projection
14b: intermediate projection
14c: bottom projection
L14a: outer diameter of first projection
L14b: outer diameter of intermediate projection
L14c: outer diameter of bottom projection
14af: annular flat portion of first projection
14ag: top curved surface portion of first projection
14ah: bottom curved surface portion of first projection
H14af: width of annular flat portion of first projection
14bg: top curved surface portion of intermediate projection
14bh: bottom curved surface portion of intermediate projection
14cg: top curved surface portion of bottom projection
14ch: bottom curved surface portion of bottom projection
15a, 15b: annular valley
L15a, L15b: outer diameter of annular valley
15aj, 15bj: curved surface portion of annular valley

The invention claimed is:

1. A gasket, having at least two annular projections and at least one annular valley on a sliding surface,
    the sliding surface comprising immobilized polymer chains,
    the annular projections including a first projection nearest to a top surface and any other projection,
    outer diameters of the other projection and the annular valley being in the range of 94 to 98% and 85 to 92%, respectively, with respect to an outer diameter of the first projection taken as 100%,
    wherein the first projection has a curved surface portion on both its top and bottom sides, and the curved surface portion on the top side has a curvature of 0.1 to 0.4.

2. The gasket according to claim 1,
    wherein the at least two annular projections comprise at least three annular projections, including the first projection, a bottom projection nearest to a bottom surface, and an intermediate projection located between the first projection and the bottom projection, and
    the intermediate projection has a smaller outer diameter than both the first projection and the bottom projection.

3. The gasket according to claim 1,
    wherein the first projection has a curved surface portion on both its top and bottom sides, and
    the curved surface portion on the bottom side has a greater curvature than the curved surface portion on the top side.

4. The gasket according to claim 1,
    wherein the other projection has a curved surface portion on both its top and bottom sides, and
    the curved surface portion has a curvature of 0.2 to 0.8.

5. The gasket according to claim 1,
    wherein the annular valley has a curved surface portion, and
    the curved surface portion has a curvature of 0.4 to 2.0.

6. The gasket according to claim 1,
    wherein the first projection has an annular flat portion having a width of 0.05 to 0.3 mm.

7. The gasket according to claim 1,
    wherein the polymer chains are immobilized by a surface modification method comprising:

step 1 of forming polymerization initiation points A on a surface of a gasket base material; and step 2 of radically polymerizing a monomer starting from the polymerization initiation points A to grow polymer chains.

8. The gasket according to claim 7, wherein the surface modification method comprises:

step 3 of extending each polymer chain grown in step 2 by adding the same or a different polymer chain; or step 3' of attaching a silane compound to a surface of each polymer chain grown in step 2, followed by reaction with a perfluoroether group-containing silane compound to grow a functional polymer chain.

9. The gasket according to claim 7, wherein step 1 comprises adsorbing a photopolymerization initiator A onto the surface of the gasket base material, optionally followed by irradiation with LED light having a wavelength of 300 to 450 nm, to form polymerization initiation points A from the photopolymerization initiator A on the surface.

10. The gasket according to claim 7, wherein step 2 comprises radically polymerizing a monomer starting from the polymerization initiation points A by irradiation with LED light having a wavelength of 300 to 450 nm to grow polymer chains.

11. The gasket according to claim 1, wherein the polymer chains are immobilized by a surface modification method comprising step I of radically polymerizing a monomer in the presence of a photopolymerization initiator A on a surface of a gasket base material to grow polymer chains.

12. The gasket according to claim 11, wherein the surface modification method comprises:

step II of extending each polymer chain grown in step I by adding the same or a different polymer chain; or step II' of attaching a silane compound to a surface of each polymer chain grown in step I, followed by reaction with a perfluoroether group-containing silane compound to grow a functional polymer chain.

13. The gasket according to claim 11, wherein step I comprises radically polymerizing a monomer by irradiation with LED light having a wavelength of 300 to 450 nm to grow polymer chains.

14. The gasket according to claim 1, wherein a total polymer chain length is 10 to 50,000 nm.

* * * * *